United States Patent [19]

Gereg

[11] 4,361,107
[45] Nov. 30, 1982

[54] OVERINFLATION INDICATOR FOR TRACHEAL TUBES

[76] Inventor: Gordon A. Gereg, 557-A Blue Church Rd., Coopersburg, Pa. 18036

[21] Appl. No.: 208,655

[22] Filed: Nov. 20, 1980

[51] Int. Cl.³ .................... G01P 3/00; A61M 25/00
[52] U.S. Cl. .................................. 116/266; 116/270; 116/DIG. 7; 116/DIG. 8; 116/DIG. 21; 128/207.15; 604/100
[58] Field of Search .............. 128/202.22, 205.23, 128/207.15, 349 B; 116/270, 266, DIG. 7, DIG. 8, DIG. 9, DIG. 21, 210; 73/731, 146.8, 715, 744

[56] References Cited

U.S. PATENT DOCUMENTS

| 2,977,973 | 4/1961 | Chakine | 116/DIG. 9 |
| 3,731,691 | 5/1973 | Chen | 128/207.15 |
| 4,136,560 | 1/1979 | Gellos | 73/146.8 |

Primary Examiner—Henry J. Recla

[57] ABSTRACT

A pressure indicating device for use with medical cannulae having balloon type sealing cuffs such as tracheal tubes. The device would be added to a normal pilot balloon to indicate having exceeded a preset pressure by having a long tubular structure that could be folded inside itself telescopically at low pressure and would pop-out at the preset pressure. When elongated or popped-out, a visual indicator would be exposed until the overpressure was corrected and the tube again tucked into itself.

5 Claims, 4 Drawing Figures

OVERINFLATION INDICATOR FOR TRACHEAL TUBES

FIELD

Surgery, Cannula

Tracheal tubes are PVC tubes used to convey gases to the lungs by way of the mouth, nasal passage, or a surgical incision in the trachea. To allow positive pressures, a sealing cuff is provided at the end positioned in the trachea. This cuff usually takes the form of a thin balloon attached to the outer diameter of the main tube and filled with air to make a seal against the walls of the trachea. A low sealing pressure is desirable to avoid tissue damage making sensitive indicators necessary.

A small hole or lumen is provided in the wall of the main tube and this hole is extended by a small tube so the sealing cuff shares air pressure with the inflation indicating balloon. The inflation indicating balloon is needed since the sealing cuff cannot be seen or touched when it is in place.

When used with anesthesia gases the cuffs on the tracheal tubes often allow gas to pass into them due to the difference in partial pressures of nitrous oxide for example and air. This diffusion in without diffusion out increases the sealing pressure of the cuff which can cause damage to the trachea. A watchful user will check the pressure in the system by feeling or gauging the inflation indicator and let gas out if necessary.

Patients are often fitted with a cuffed tube for extended periods which may be weeks in the case of a tracheostomy tube. With the present invention the problem of many people having to monitor the same patient and not being sure of the cuff pressure is eliminated. Often a clinician will add a little pressure to be sure there is a seal which results in overpressure. Gauges are available to check the exact pressure but they are inconvenient to use and often are inaccurate because their connection tubing has considerable volume and damps or reduces the pressure reading. Also more connections increase the possibility of leaks.

Long term patients have the greatest chance for tracheal damage from overpressurized sealing cuffs. A failure of the cuff seal due to pressure loss could result in a loss of air to the patient.

The present design is intended to give a more positive warning of overpressure. Also it would require resetting which could only be done if the pressure was in the proper range. Earlier designs have a less dramatic change with pressure or work in a higher pressure range.

The lower part of the indicator (below the valve mounting area) would be the same as any of a number of indicators presently used. In fact, if the system was never overpressurized it would be difficult to notice there was an extra feature on the indicator. Commonly used syringe valves such as the Halkey-Roberts 810 ACA could be part of the new design also.

Instead of mounting the syringe valve directly into the balloon of the indicator, a long thin tube or neck would be provided between the balloon and the indicator. The new feature would substantially improve on present inflation indicating devices while adding little or nothing to the cost.

For PVC indicators, the neck would be about 0.008 inch thick and the effective length would be about twice the valve length. The pop-out of the syringe valve would work best if the valve was mounted in a special way so the long tube would easily fold over itself. For more flexible materials such as silicone rubber or urethane the thickness could be less assuming a satisfactory strength was obtained.

Only about ⅛ inch of the valve would be inserted into the partially folded tube and the valve would be sealed to the tube. The valve would then be pushed into the tube as the tube folded back on itself.

After the seal was made the valve could be pushed into the neck of the balloon so the resulting assembly would look quite normal. Under normal use conditions the valve would stay tucked into the neck. If the assembly were to be overpressurized, the neck would blow up slightly making it easy for the valve to pop-out to its extended position in piston fashion. The outer diameter of the valve body in the area above the seal to the balloon neck could be printed with a bright color or a bright piece of tape applied. If the neck was opaque, the bright color would only be visible when the neck was extended which would further call attention to the overpressurized state. The neck section could be made as a separate piece and bonded to both the valve and the balloon.

By adjusting the thickness and hardness of the balloon material in the neck area, the pressure at which the valve would pop-out could be adjusted. The lubricity of the inner surface of the neck also will effect the pop-out pressure. The action making the pop-out feature release is the circumferential expansion of the neck area which makes it easy for the pressure to force the valve outwards even though the pressure involved is only in the range of 25 cm of water. Other indicating devices have less dramatic physical changes for small pressure differential. This feature also allows use of materials that are relatively stiff or thick and have minimal lubricity. An important feature is the fact the pop-out action is sudden rather than gradual.

These and other objects will be apparent from the following specification and drawings, in which.

Figure 1:
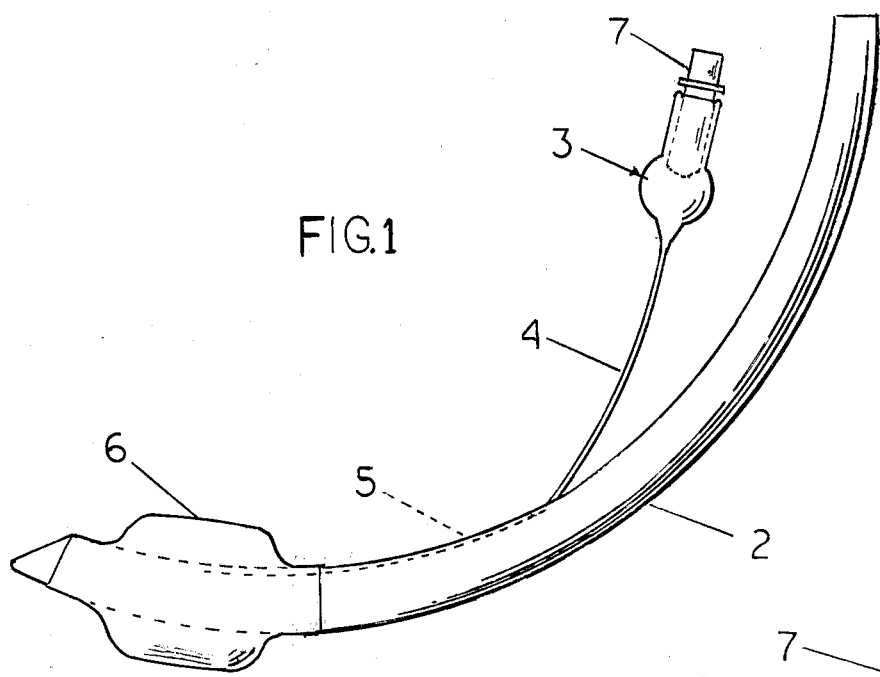
FIG. 1 is a perspective view of a complete tube with an inflation indicating balloon.

Referring now to the drawings, in which like reference numerals denote similar elements, a complete tracheal tube 2 is shown in FIG. 1 with a typical inflation indicating balloon 3 which may have the feature of the invention although it would not be apparent because it is not shown activated. The inflation indicating balloon 3 is connected with a small tube 4 to a lumen in the wall of the main tube 5 which causes the interior of the inflation indicating balloon 3 to be connected with the interior of the sealing cuff 6 which covers a notch accessing the lumen in the wall. In this manner any air pressure in the cuff 6 is the same as the pressure in the inflation indicating balloon 3. A tube of the type referred to as an endotracheal tube which inserts through the mouth into the tracheal is shown and discussed as an example although the invention is equally applicable to other types of cuffed tubes such as nasal tubes or tracheostomy tubes. Note that a syringe valve 7 is provided to allow air to be added or taken out using a common medical syringe having a luer tip.

To produce an inflation indicator balloon a plastisol dipping process is commonly used which forms a balloon by dipping a shaped mandril into liquid plastic and heating the plastic to solidify it. The balloon is then cooled and stripped from the mandril. Other means such as slush molding or blow molding could be used. Other liquidified processing such as rubber vulcanizing also might be used.

Figure 2:
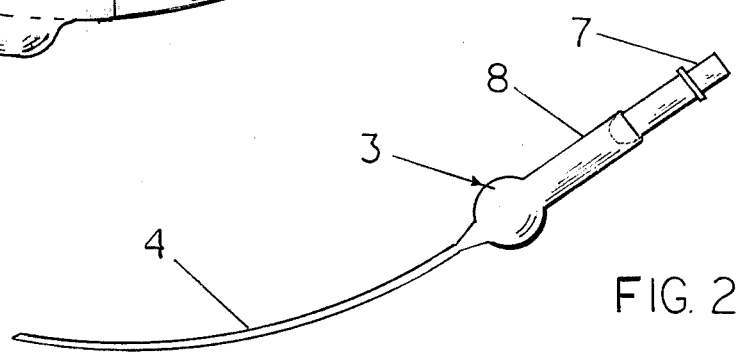
FIG. 2 is a perspective view of an inflation indicating balloon with the pop-out extended.
Figure 3:
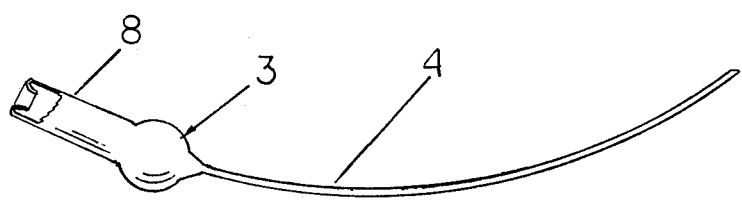
FIG. 3 is a sectional view showing the neck detail of an inflation indicating balloon.

Given a balloon shape with a sufficiently long neck 8, the preferred method of installing the valve 7 into the neck 8 is by first starting to fold the neck inside itself as shown in FIG. 2. The valve 8 would only be bonded in a thin band near the tip and would be bonded to that part of the neck 8 that was the upper end of the outside of the neck 8 before it was folded in as shown in FIG. 3. By using this bonding arrangement the pop-out feature would be more sensitive to small pressure changes. The device would work nearly as well for thin materials if the top of neck 8 was left unfolded and the valve merely inserted a short way and bonded by a suitable means.

The shape of the inflation indicating balloon 3 could be round, oval or semiflat in cross section and any convenient shape in the plane dimension. The size of the balloon portion, that is the wider section not including neck 8, would have to be suited to adapting the diameter of the valve. It may be desirable to make the neck 8 short so that when the valve 7 were popped in it would actually be inside the balloon portion. This would make the overall length of the inflation indicator shorter and would also position the valve closer to the small tube 4 that is the outlet from the balloon. Having the valve 7 closer to the small tube 4 will make a shut off of air flow less likely if the air is pulled rapidly out of the balloon which could cause the balloon to collapse around the valve 7. Enough neck 8 would be needed to insure expansion could occur to release the valve 7 for the pop-out action.

Figure 4:
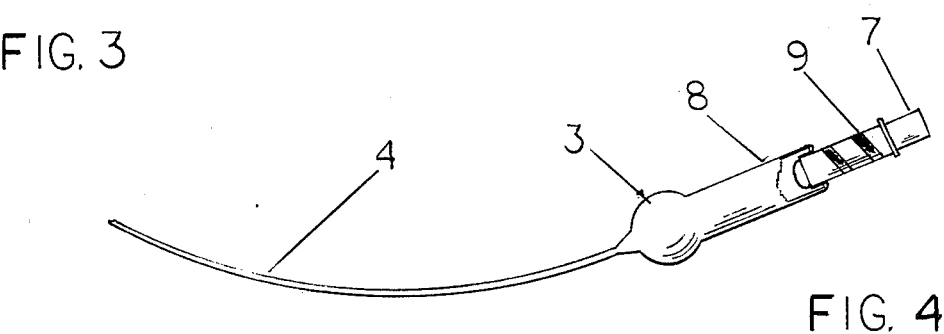
FIG. 4 is a sectional view of the neck detail of an inflation indicating balloon showing the seal to a syringe valve.

The entire inflation indicating balloon 3 could be made of an opaque material, or as an alternative, only the neck 8 could be opaque. The reason for making at least the neck opaque is so the valve 7 could have a band 9 of contrasting color applied such as by taping or painting that would not be visible when the valve 7 was tucked in the neck. The band 9 would be only visible when the valve 7 was popped-out and would be an additional means of attracting attention to the overpressure that was in effect. FIG. 4 shows the inflation indicator balloon 3 with the neck 8 extended and valve 7 out to a position where band 9 is showing. It is expected the valve 7 would always move to its fully extended position once it started to move since the force to overcome static friction is more than the force for the dynamic case.

To use the invention a user would be presented the tube 2 having the inflation indicating balloon as in FIG. 1 with the valve 7 tucked in. After the tube 2 was in place in a patient, the cuff 6 would be inflated by putting air in at valve 7 with a syringe. The amount of air pressure in cuff 6 and therefore, the inflation indicating balloon 3, would be less than the amount needed to cause the valve 7 to pop-out if the user was following good medical practice.

During the course of use if nitrous oxide or some other gaseous agent having a partial pressure less than air was being used it would be on only one side of the sealing cuff 6 in the patient's lower airway and lungs. It would be expected that some of the gas would diffuse into the cuff 6 raising the pressure in the cuff 6. When this occurred, the pressure in the inflation indicating balloon 3 would also rise. When the pressure reached a predetermined safe limit, for example 20 cm of water, the neck 8 of the device would grow in diameter until it was larger than the outer diameter of the valve 7 making it very easy for the valve 7 to pop-out to its extended position due to the piston effect of the pressure on the end of the valve 7. A watchful user would notice the overpressurized state and remove some air by withdrawing it through valve 7 with a syringe. The valve 7 and neck 8 could then be returned to an inward position to be available for indication of later overpressurization.

There are other causes of overpressurization such as a change in cuff position. The most likely cause of overpressurization is improper technique of the user.

The pressure at which the pop-out indication would be activated would be predetermined by the thickness, flexibility and lubricity of the neck tube 8 and how tightly the valve body 7 fit into the folded neck tube 8. A tighter fit of the valve 7 to the neck 8 would require more pressure to expand the tube 8 and release the valve 7. In a like manner, less flexibility or less lubricity would also mean a higher pressure was needed to pop-out the valve 7.

I claim:

1. A pressure indicating device suitable for use with medical cannulas having inflatable sealing cuffs, said device including an inflation indicating balloon capable of holding a predetermined pressure and having a first port adapted to be fluidically connected to an inflatable cuff of a medical cannula and an opposite second port, an elongated tube of thin flexible material having one end secured to said balloon about said second port and an opposite end, said elongated tube having a first portion adjacent said first end and a second portion adjacent said second end, said second portion being folded inside said first portion such that said one and opposite ends extend in the same direction, cylindrical valve means adapted to receive a conventional cuff inflating device, said valve means having a first end inserted into said second portion of said elongated tube and sealed to said second end thereof, said valve means having an opposite end extending from said first and second portions of said elongated tube, said first and second portions being snugly fit around said valve means wherein a pressure in said balloon above said predetermined level causes the first portion of said tube to expand away from said second portion and causes said valve means to extend from within said first and second portions thereby indicating an overpressure condition.

2. An inflation indicating device as in claim 1 wherein said tube being thin and flexible enough to be turned inside itself easily when mounted to a conventional cuff inflating device.

3. An inflation or pressure indicating device as in claim 1 wherein said tube being made opaque and said cylindrical valve means being attached to said tube at a small band near said opposite end thereof and being tucked into the tube to be thereby hidden from sight under normal conditions.

4. A pressure indicating device as in claim 1 wherein said one end of said valve means being colored in contrast and which may be reset when the pressure is reduced.

5. A pressure indicating device as in claim 1 which can be designed to signal when a certain pressure is reached by adjusting the properties and diameter of said elongated tube used to mount said valve means which is held in said tube by interference fitting or friction until expansion releases it.

* * * * *